United States Patent
Jesseph et al.

(10) Patent No.: US 9,681,886 B2
(45) Date of Patent: Jun. 20, 2017

(54) DEVICE AND METHOD FOR IMPROVED SURGICAL INCISIONS

(71) Applicant: Jerry Jesseph MD, Bloomington, IN (US)

(72) Inventors: Jerry Jesseph, Bloomington, IN (US); Frederick Jesseph, Bloomington, IN (US)

(*) Notice: Subject to any disclaimer, the term of this patent is extended or adjusted under 35 U.S.C. 154(b) by 153 days.

(21) Appl. No.: 14/678,603

(22) Filed: Apr. 3, 2015

(65) Prior Publication Data

US 2015/0282831 A1 Oct. 8, 2015

Related U.S. Application Data

(60) Provisional application No. 61/995,264, filed on Apr. 7, 2014, provisional application No. 62/122,890, filed on Nov. 3, 2014.

(51) Int. Cl.
*A61B 17/3211* (2006.01)
*A61B 17/3213* (2006.01)
*A61B 17/00* (2006.01)

(52) U.S. Cl.
CPC ... *A61B 17/3211* (2013.01); *A61B 2017/0023* (2013.01); *A61B 2017/32113* (2013.01)

(58) Field of Classification Search
CPC ...... A61B 17/3211; A61B 2017/32113; A61B 2017/0023
USPC ................................... 30/286, 289
See application file for complete search history.

(56) References Cited

U.S. PATENT DOCUMENTS

| | | | | |
|---|---|---|---|---|
| 2,650,424 A | * | 9/1953 | Kalmon | A22B 5/168 30/286 |
| 2,730,800 A | * | 1/1956 | Bailey | B26B 5/006 30/153 |
| 2,743,523 A | * | 5/1956 | Honey | B26B 5/006 30/2 |
| D535,026 S | * | 1/2007 | Griffin | A61B 17/3211 D24/146 |
| D561,898 S | * | 2/2008 | Goto | A61B 17/3211 D24/146 |
| 7,341,596 B2 | | 3/2008 | Heppler | |
| 7,900,362 B2 | | 3/2011 | Djordjevic et al. | |
| 8,819,945 B2 | * | 9/2014 | Reibold | B26B 29/02 30/2 |
| 8,875,405 B2 | * | 11/2014 | Trees | A61B 17/3211 30/151 |
| 2009/0131963 A1 | * | 5/2009 | Rasco | A61B 17/3213 606/172 |
| 2012/0130165 A1 | * | 5/2012 | Riva | A61B 17/32002 600/104 |
| 2013/0192069 A1 | * | 8/2013 | Reibold | B26B 1/10 30/295 |
| 2014/0207188 A1 | * | 7/2014 | Yearsley | A61B 17/06109 606/224 |

(Continued)

*Primary Examiner* — Hwei C Payer
(74) *Attorney, Agent, or Firm* — C. John Brannon; Brannon Sowers & Cracraft PC

(57) ABSTRACT

A disposable scalpel, including a body portion having a proximal end and a distal end, a scalpel blade receiving slot formed in the distal end, and first and second parallel elongated flexible members, wherein the slot is positioned between the pair of parallel elongated flexible members, such that a scalpel blade received in and extending from the slot would be flanked by the pair of parallel elongated members.

3 Claims, 7 Drawing Sheets

(56) References Cited

U.S. PATENT DOCUMENTS

2015/0282831 A1* 10/2015 Jesseph .............. A61B 17/3211
606/167

* cited by examiner

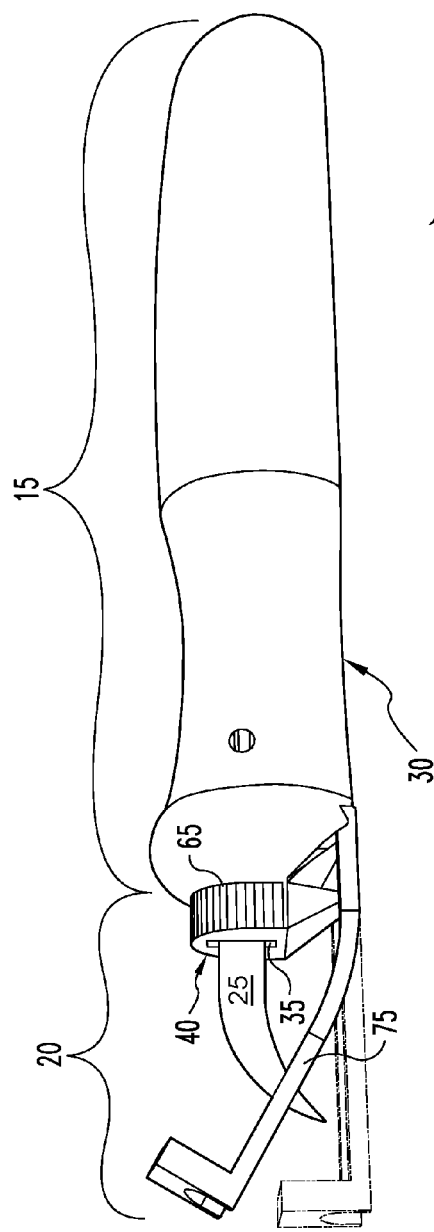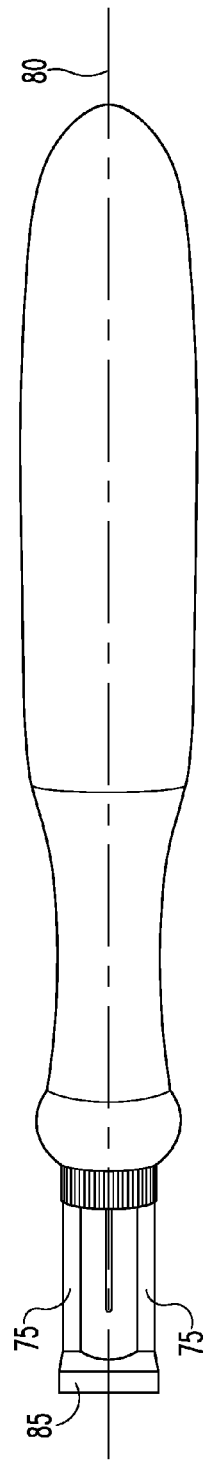

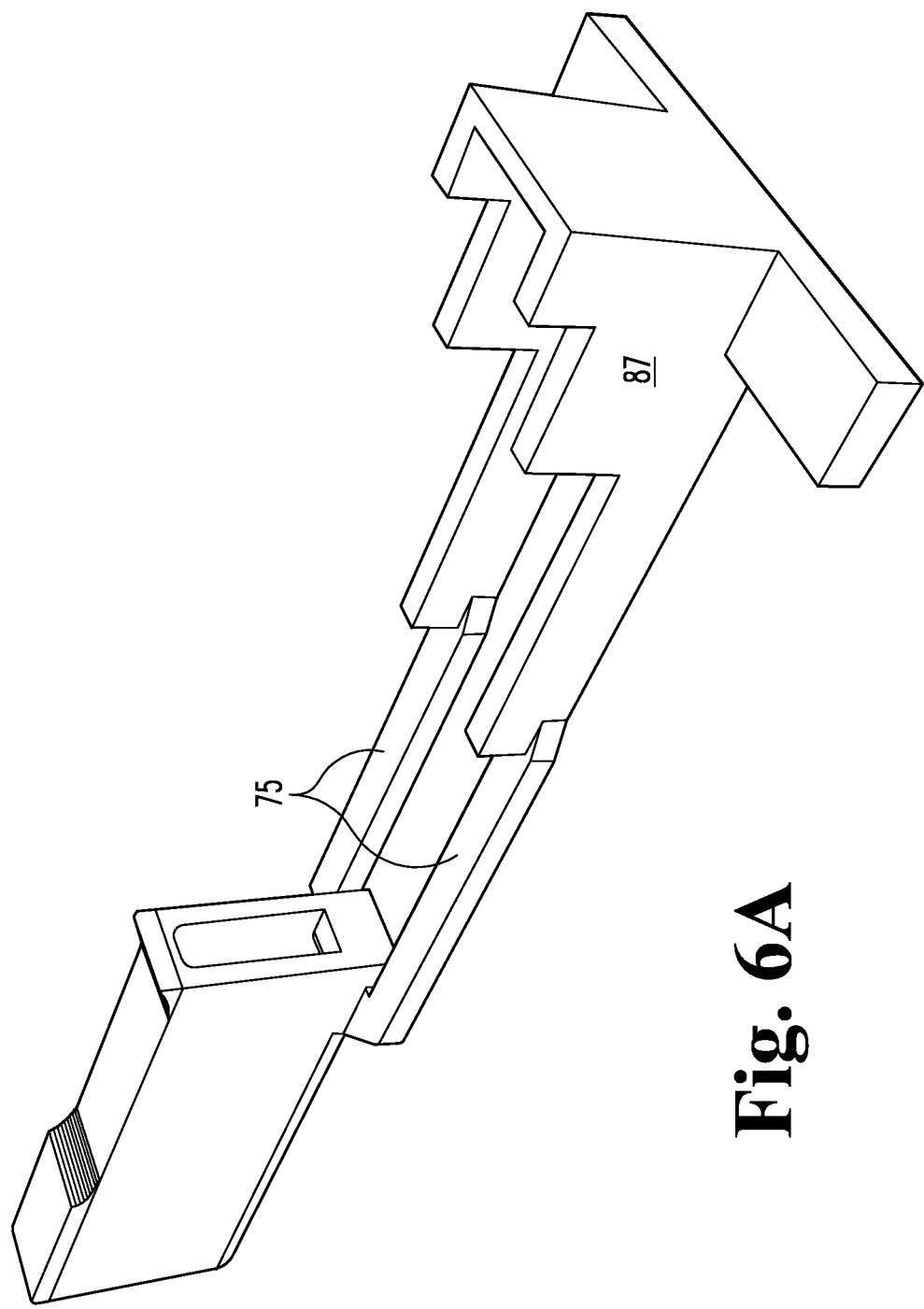

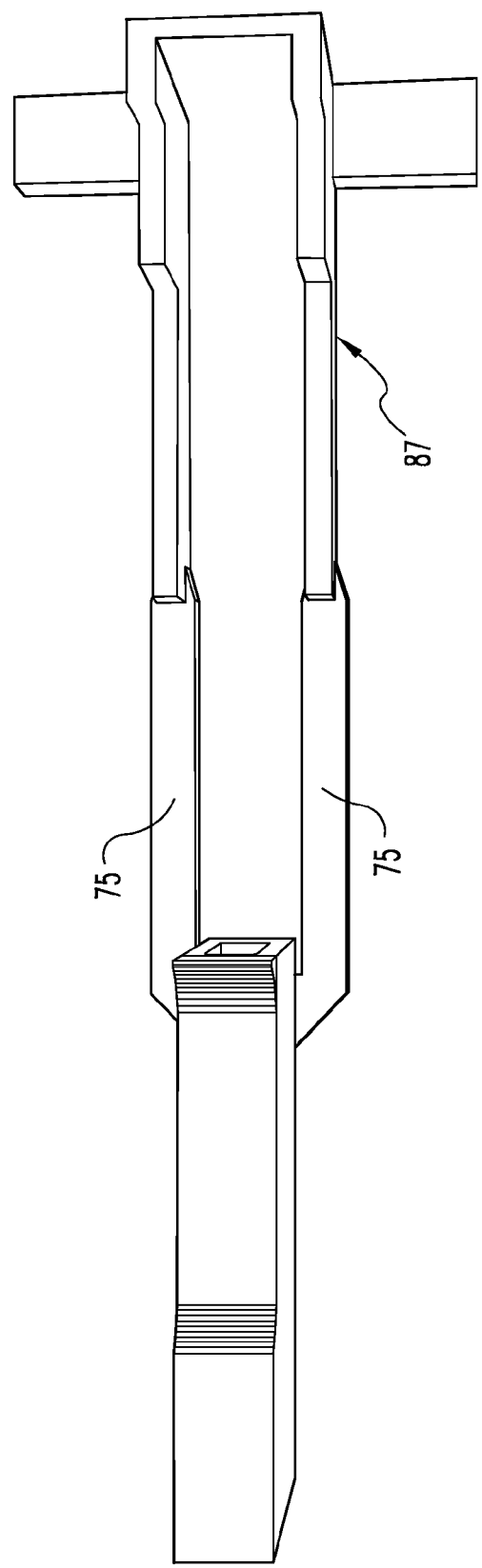

DEVICE AND METHOD FOR IMPROVED SURGICAL INCISIONS

CROSS-REFERENCE TO RELATED APPLICATIONS

This patent application claims priority to U.S. provisional patent application Ser. No. 61/995,264, filed on Apr. 7, 2014, and to U.S. provisional patent application Ser. No. 62/122,890, filed on Nov. 3, 2014, both of which are incorporated herein by reference.

TECHNICAL FIELD

This novel technology relates generally to the field of surgical instruments and, more particularly, to a disposable scalpel.

BACKGROUND

The most commonly used currently available surgical scalpels were designed over 100 years ago and were first granted a patent in 1915. For more than a century, little substantive design improvement has been made. The standard surgical scalpel is still comprised of an elongated handle, usually made of metal, into which a detachable and disposable cutting blade is inserted. While a few modifications of this basic design have been suggested, none has gained acceptance and wide usage by surgeons.

While the old scalpel design has hung on, surgical scalpel injuries to patients, surgeons, and operating room personnel remains the second most common, and arguably most avoidable, healthcare injury after accidental needle sticks worldwide. Concerns for continued risk and injury from scalpels were expressed by the United States Congress in The National Needle Stick Prevention Act.

While there are some, typically disposable, known scalpel designs with an added feature of a guard for covering the sharpened part of the scalpel blade when not in use and/or wherein the blade can be retracted into the handle, as protective devices requiring attentive activation, these methods are still wanting in actually protecting patients and surgical teams from unintended harm as the safety protocols must be disengaged for the scalpel to be used. Further, the presence of a prior art scalpel guard diminishes the skill that can be brought to bear by the surgeon, and thus interferes with the efficacy of the scalpel.

Thus, there is a need for a scalpel having a safety feature to prevent accidental and unintended injury while also not detracting from the skill and ability of the surgeon. The present novel technology addresses this need.

BRIEF DESCRIPTION OF THE DRAWINGS

FIG. 3 is a side elevation view of the disposable scalpel of FIG. 2.

FIG. 4 is a top plan view of the disposable scalpel of FIG. 1.

FIG. 6A is a perspective view of an extension assembly for the scalpel of FIGS. 1-5.

FIG. 6B is a top plan view of FIG. 6A.

DETAILED DESCRIPTION

Figure 1:
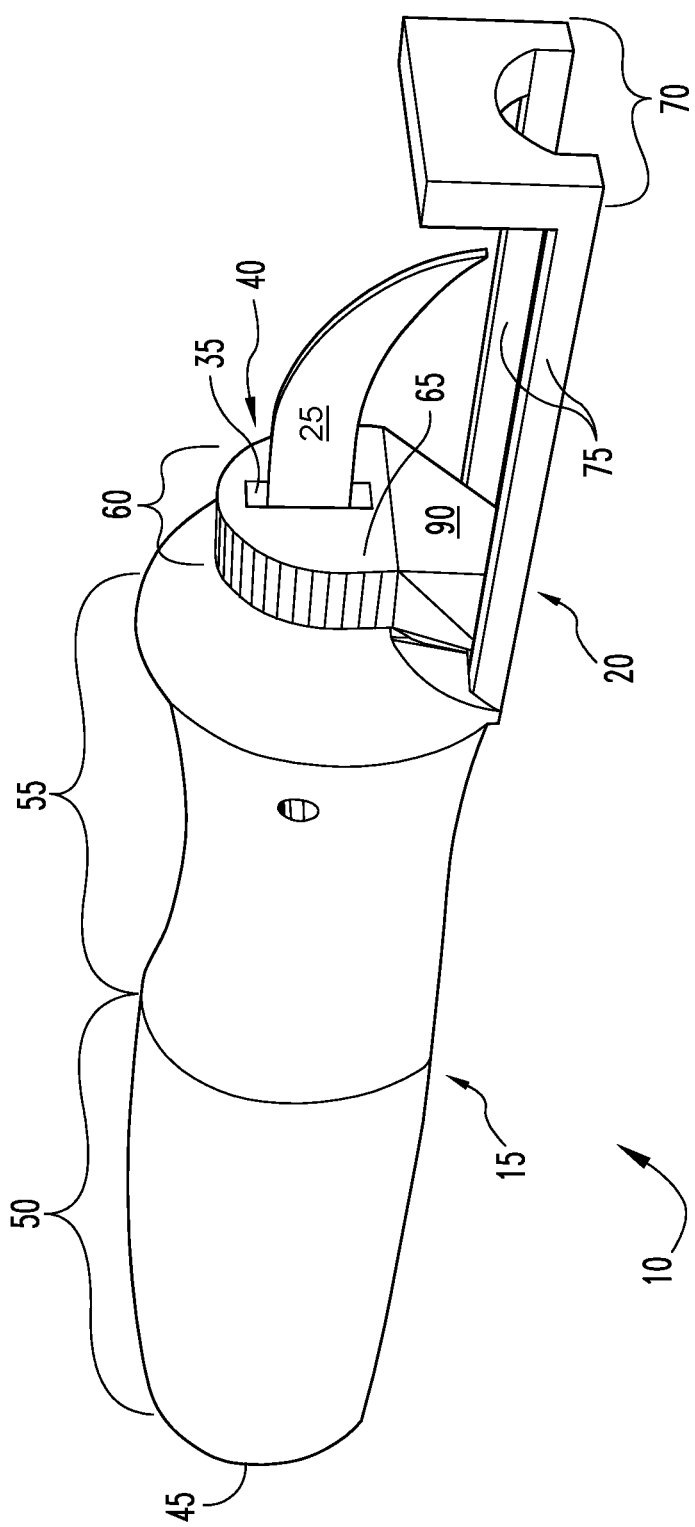
FIG. 1 is a first perspective view of one example of a disposable scalpel.
Figure 2:
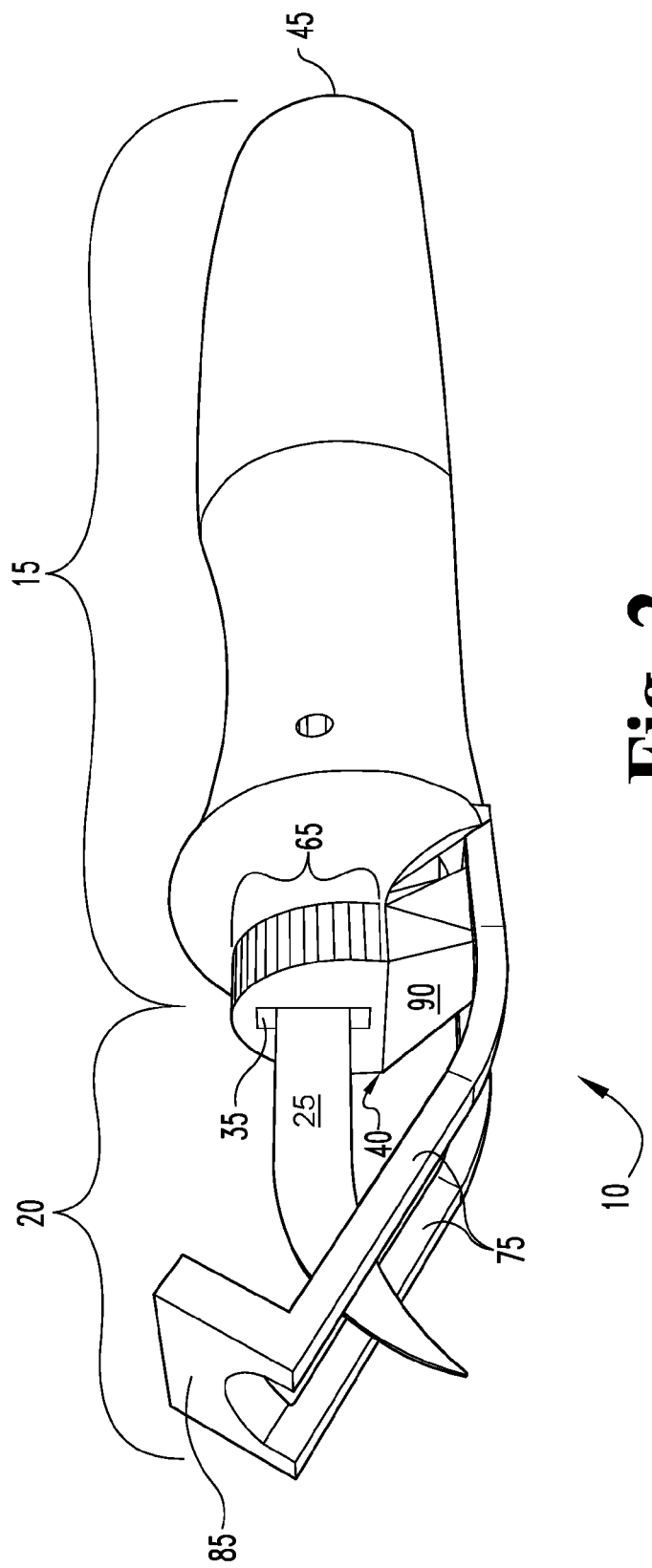
FIG. 2 is a second perspective view of the disposable scalpel of FIG. 1.
Figure 5:
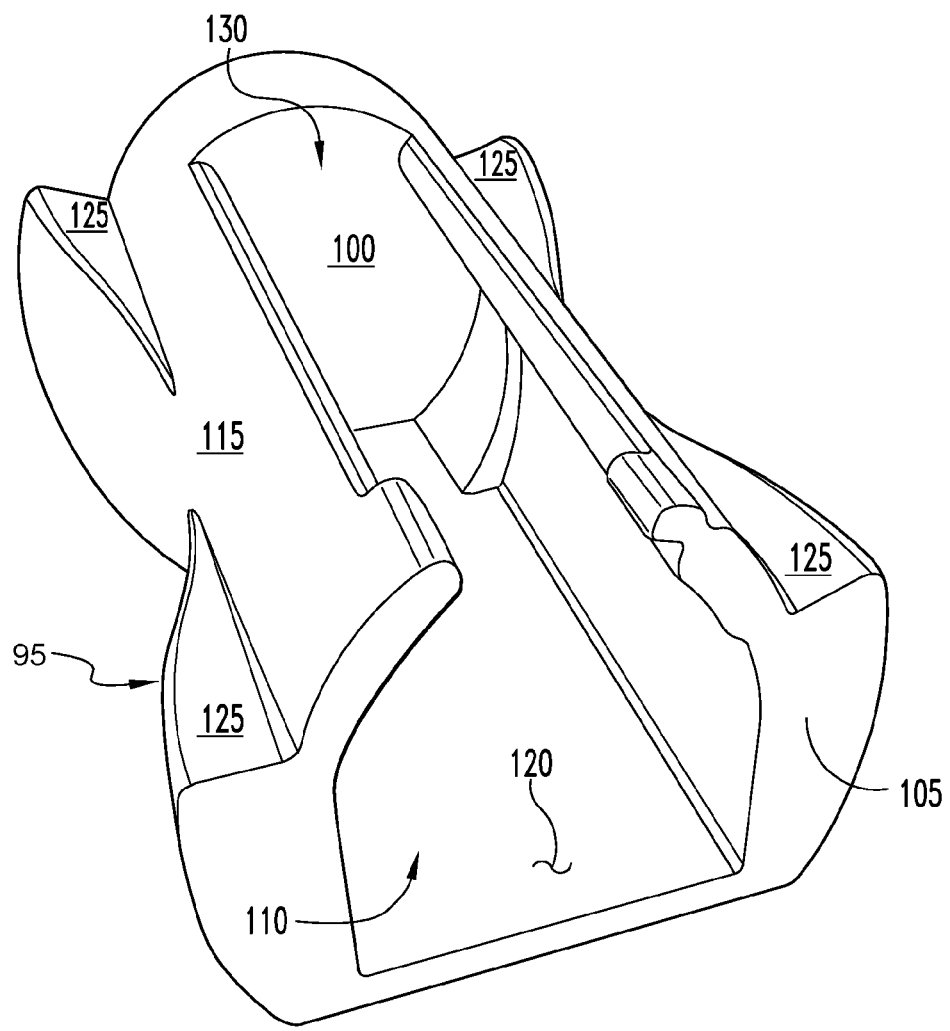
FIG. 5 is a top perspective view of a cover portion engagable to the disposable scalpel of FIGS. 1-4.

For the purposes of promoting an understanding of the principles of the claimed technology and presenting its currently understood best mode of operation, reference will now be made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would normally occur to one skilled in the art to which the claimed technology relates.

FIGS. 1-6B illustrate a first embodiment of the present novel technology, a scalpel assembly 10 including a proximal handle portion 15 and a distal blade protection/guide portion 20 positioned to extend from the handle portion 15 parallel with a scalpel blade 25 when such a blade is operationally connected to the handle portion 15. The handle portion 15 is typically formed of a lightweight structural material, such as plastic, and is more typically a 3D printed piece. The handle portion 15 typically has a flat bottom side 30, such that it may be set down in an upright orientation with the scalpel blade edge facing downwardly when not in use, in contrast to traditional scalpels having to be laid down on their sides with the blade edge facing out instead of down.

The handle portion typically has a blade-receiving slot 35 formed in the distal end 40 for snugly accepting the insertion slot of a standard scalpel blade. Extending from the oppositely disposed proximal end 45 toward the distal end 40 for approximately half the length of the handle portion, is the slightly outwardly or convexly bulged proximal portion 50. Adjacent the proximal portion 50 is the distal portion 55, extending from about the midpoint of the handle portion 15 and characterized by a convex or inwardly bulging curvature. The distal portion 55 terminates in an outwardly bulging, generally donut shaped distal end portion 60 to which is typically attached a typically knurled and typically arch-shaped connecting portion or terminus 65.

While the handle portion 15 is described above according to the details of this specific embodiment, the handle portion may have any convenient ergonomic design.

The blade guard/guide portion 20 includes the connecting portion 65 and scalpel guide frame 70 made up of a pair of elongated parallel flexible members 75 extending parallel to the major axis 80 of the handle portion 15. The elongated members 75 are typically parallel to a scalpel blade when engaged in the slot 35 and extending therefrom, and are likewise typically positioned to be equidistant from such a blade. The elongated members 75 are elastically flexible, such that they may be deformed from their initial elongated linear shape into a curved shape with application of moderate force, such as that of a surgeon pressing the scalpel blade into flesh, and offer spring resistance such that upon removal of the applied force the elongated members 75 resume their initial elongated linear shape. The elongated members 75 extend from the handle portion 15 and typically terminate in a transverse bridge member 85 extending between the elongated members 75 and connecting the same. In this embodiment, the end bridge member 85 typically has a flat top and an arched bottom to facilitate usage of the scalpel blade, although the bridge 85 may have any convenient shape. In some embodiments, the bridge member 85 includes one or more generally flat elongated stabilizing members 87 extending transversely therefrom (see FIG. 6A-6B). In some embodiments, the bridge member 85 is connected to the extended members 75 by a pair of parallel intermediate elongated members (not shown) extending from the bridge member 85 to reengagably removably engage the respective elongated members 75. In this embodiment, the stabilizing members 87 and intermediate members act as a locking mechanism to restrain the elongated members or rails 75 from bending or otherwise deforming. This feature requires either disengagement or additional active pressure by the operator to allow the rails 75 to bend. If additional pressure is not provided, the rails 75 will not bend and, therefore, the sharp portion of the blade is prevented from engaging either the patient or anyone else's flesh.

The presence of the rails 75 allows for more precise surgical incisions largely independently of skill of the operator. The parallel elongated rails 75 and their biasing feedback force give the surgeon an additional tool for producing precision incisions that are clean, straight and at right angles to allow for additional benefits of better healing, better scarring and fewer complications such as infection, delayed healing, dehiscence, keloid and the like.

A wedge member 90 is typically positioned between the connecting member 65 and the elongated members 75 at the end of the handle portion 15 to provide support for the elongated members 75. The elongated members 75 may include skids, plates, platforms or the like that act to stabilize skin, sub-cuticular and/or surrounding anatomic and surgical field structures to more reliably enable reproducible, precise incisions.

The entire assembly 10 is typically unitarily formed and is more typically a lightweight, 3D printed plastic piece.

Some embodiments include an elongated detachable scalpel blade cover 95 having a solid distal end wall 100, a proximal end wall 105 defining an opening no for engaging the lockingly distal end portion 60, and an elongated contoured body wall 115 extending therebetween. The elongated contoured body wall 115 typically further defines a flat bottom portion 120, contoured side portions 125 and an open slotted top portion 130. The blade cover 95 is likewise typically formed from light plastic and is more typically 3D printed. The opening 110 is shaped to matingly accept the distal end portion 60, with the bottom portions 120, 30 aligned. The blade cover 95 likewise performs the function of a locking member as described above, preventing the rails 75 from bending while engaged.

Figure 7:
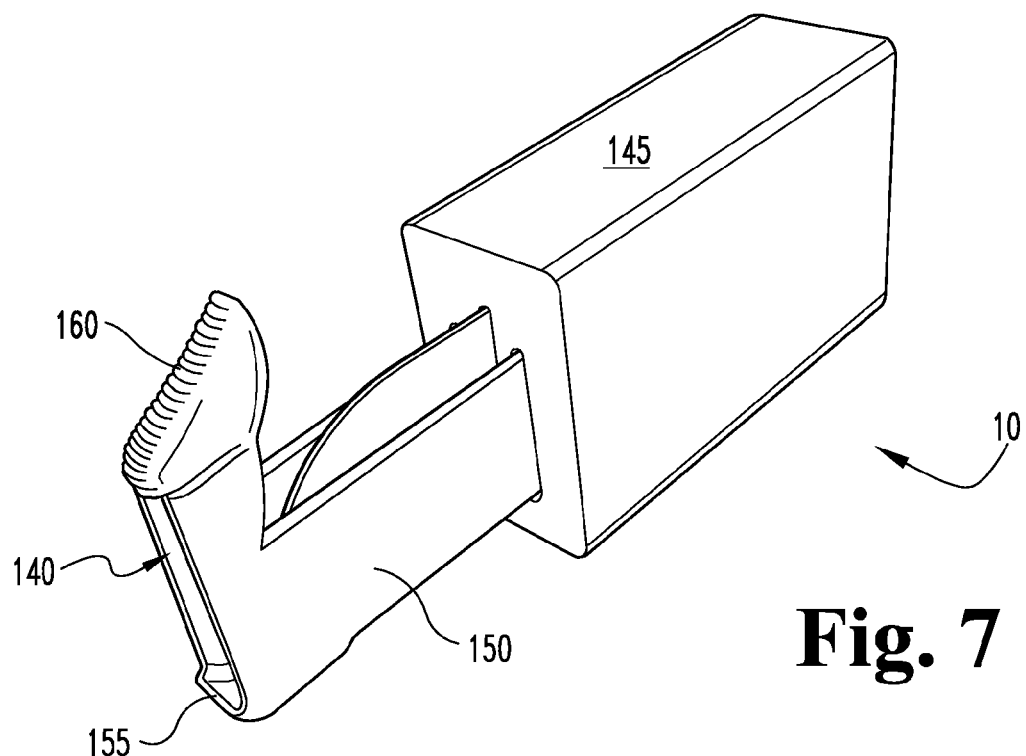
FIG. 7 is a perspective view of a second embodiment disposable scalpel of the present novel technology.
Figure 8:
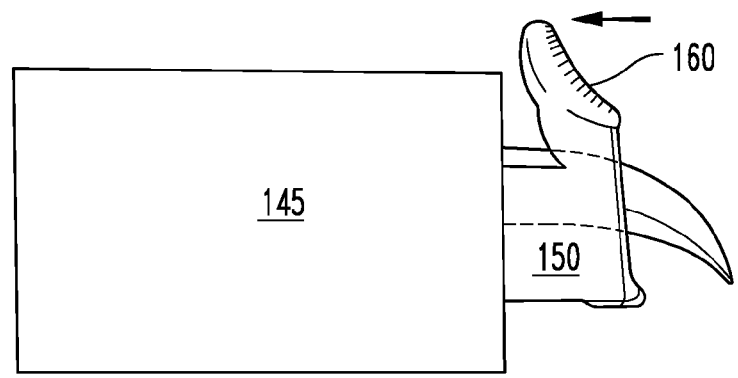
FIG. 8 is a side view of the scalpel of FIG. 7 with the side walls partially retracted to expose the scalpel blade.

Some embodiments include a retractable scalpel shield member 140 operationally connected to the distal end 40 of the handle portion 15 (see FIGS. 7-8). The retractable scalpel shield member 140 typically defines a hollow housing 145 comprising a pair of parallel sidewalls 150 extending parallel the with scalpel blade and parallel with the major axis 80, and a bottom member 155 extending therebetween to prevent accidental contact with the sharp edge of the blade. The housing 145 is retractable into the handle portion 15, and includes a thumb grip portion 160 extending therefrom for urging the housing 145 into the handle portion 15 to expose the scalpel blade for surgical use. A biasing member or spring (not shown) is operationally connected to the housing portion 145 to urge it out of the handle 15 and around the scalpel blade as its default position, unless manually retracted by the surgeon. The biasing member is typically positioned within the handle portion 15 and operationally connected to the housing 145. In other words, the housing portion 145 remains locked or deployed in a position covering the sharpened portion of a scalpel cutting edge at all times except when the device 10 is in use cutting. The housing portion 145 requires active and continuous deactivation of the biasing member by the operator while in use.

In operation, the blade guard 20 is placed against a patient's skin and the sharpened portion of the blade 25 protrudes below the rails 75 as the rails bend, making a cut having a depth dependent on the pressure applied. Once the blade 25 has been inserted to the desired depth, the blade 25 is pulled along a desired path with the rails 75 positioned on opposing sides and parallel to the blade 25, providing a downward and outward urging force on the patient's skin to both stabilize the patient's skin and flesh and provide stabilization and guidance to the incision so made. When the blade 25 is lifted, the rails 75 straighten and again reposition below the sharp portion of the blade 25 thereby providing protection from inadvertent injuries. The rails 75 themselves act to kept the skin or surrounding material at right angles to the cutting blade 25, providing a dependably clean and right-angled cut, free from beveling, as well as lateral tissue stabilization during surgery and/or leading/trailing tissue stabilization as the scalpel is pulled forward through flesh. The entire knife assembly 10 remains in a stable upright position when placed on a surface, and thus is more safely accessible for grasping. Typically, the blade cover portion 95 is engaged during prolonged periods of disuse.

While the claimed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

What is claimed is:

1. A lightweight, disposable scalpel blade support assembly, comprising:
    an elongated, generally cylindrical handle portion defining a first major axis and having a proximal end and an oppositely disposed distal end; and
    a scalpel blade guard portion extending from the distal end;
    wherein the elongated, generally cylindrical handle portion has a flat bottom side extending parallel to the major axis;
    wherein the scalpel blade guard portion further comprises:
        a pair of elongated elastically flexible members extending parallel to the first major axis; and
        a bridge member extending perpendicularly between and connecting the pair of elongated elastically flexible members;
    a generally hollow housing portion having a first generally flat solid endwall;
    a second oppositely disposed and parallel endwall;
    an aperture extending through the second endwall;
    a flat bottom wall extending therebetween and oppositely disposed curved sidewalls extending from the flat bottom wall and extending between the first and second endwalls;

wherein the aperture is shaped to snugly accept the distal end with the pair of elongated elastically flexible members extending to engage the first endwall and positioned adjacent the bottom wall.

2. A disposable scalpel system, comprising:

an elongated handle portion defining a first major axis and having a proximal end and an oppositely disposed distal end and having a flat side extending therebetween and disposed parallel to the major axis, and further comprises:
- first and second oppositely disposed elongated members extending from the distal end;
- a slot formed in the distal end for snugly receiving a scalpel blade and positioned between the first and second elongated members;
- an elongated bridge member extending between and connecting the first and second oppositely disposed parallel elongated members; and
- a raised connecting ring formed adjacent the distal end; and a hollow, generally cylindrical end guard portion having a first solid endwall, an oppositely disposed aperture second endwall, and a slotted generally cylindrical sidewall extending therebetween;

wherein the aperture endwall is sized and shaped to matingly accept the connection ring to engage the generally cylindrical endguard portion with the elongated handle portion to substantially enclose the scalpel blade extending from the slot.

3. A method for using a scalpel, comprising:

providing a disposable scalpel, having a body portion having a proximal end and a distal end; a scalpel blade receiving slot formed in the distal end; and a first flexible elongated member extending from the distal end; a second flexible elongated member extending from the distal end; wherein the first and second flexible elongated members are disposed parallel to each other; wherein the slot is positioned between the pair of parallel elongated flexible members, such that a scalpel blade received in and extending from the slot would be flanked by the pair of parallel elongated members;

snugly engaging a scalpel blade in the slot;

engaging the scalpel blade against a patient's skin;

urging the blade into the patient's flesh while flexing the elongated members against the patient's skin;

guiding the scalpel blade through the patient's flesh using the flexed elongated members to gauge the scalpel blade's path and depth;

removing the scalpel blade from the patient by pivoting the scalpel about the flexed members.

* * * * *